(12) United States Patent
Zinn et al.

(10) Patent No.: US 8,298,215 B2
(45) Date of Patent: Oct. 30, 2012

(54) GUIDEWIRE TIPPED LASER FIBER

(75) Inventors: Kenneth Zinn, Westport, CT (US); Jeff Welch, Maple Grove, MN (US); Howard Root, Excelsior, MN (US)

(73) Assignee: Vascular Solutions, Inc., Minneapolis, MN (US)

( * ) Notice: Subject to any disclaimer, the term of this patent is extended or adjusted under 35 U.S.C. 154(b) by 1400 days.

(21) Appl. No.: 11/860,880

(22) Filed: Sep. 25, 2007

(65) Prior Publication Data

US 2009/0082760 A1    Mar. 26, 2009

(51) Int. Cl.
*A61B 18/18* (2006.01)

(52) U.S. Cl. ............... 606/15; 606/7; 128/898; 600/585

(58) Field of Classification Search .......... 606/7, 13–16; 607/88, 89, 92; 128/898; 600/585
See application file for complete search history.

(56) References Cited

U.S. PATENT DOCUMENTS

| | | | |
|---|---|---|---|
| 4,257,421 A | 3/1981 | Beal | |
| 4,553,545 A | 11/1985 | Maass et al. | |
| 4,564,011 A | 1/1986 | Goldman | |
| 4,654,028 A | 3/1987 | Suma | |
| 4,768,507 A | 9/1988 | Fischell et al. | |
| 4,771,773 A | 9/1988 | Kropf | |
| 4,848,342 A | 7/1989 | Kaltenbach | |
| 5,188,634 A | 2/1993 | Hussein | |
| 5,466,234 A * | 11/1995 | Loeb et al. | 606/15 |
| 5,855,577 A | 1/1999 | Murphy-Chutorian et al. | |
| 6,398,777 B1 | 6/2002 | Navarro et al. | |
| 7,273,478 B2 | 9/2007 | Appling et al. | |
| 2003/0181894 A1 * | 9/2003 | Neuberger | 606/15 |
| 2003/0191460 A1 | 10/2003 | Hobbs et al. | |
| 2004/0010248 A1 | 1/2004 | Appling | |
| 2005/0288655 A1 * | 12/2005 | Root et al. | 606/15 |
| 2006/0142747 A1 | 6/2006 | Appling | |
| 2008/0015559 A1 | 1/2008 | Appling et al. | |
| 2008/0188843 A1 | 8/2008 | Appling et al. | |
| 2008/0188910 A1 * | 8/2008 | Spaide | 607/89 |
| 2008/0249399 A1 | 10/2008 | Appling et al. | |
| 2008/0287939 A1 | 11/2008 | Appling | |

OTHER PUBLICATIONS

U.S. Appl. No. 11/860,880, filed Jun. 29, 2004, Howard Root et al.
U.S. Appl. No. 10/879,701, filed Jun. 29, 2004, Howard Root et al.
U.S. Appl. No. 11/648,086, filed Dec. 29, 2006, Howard Root et al.

* cited by examiner

*Primary Examiner* — Ahmed Farah
(74) *Attorney, Agent, or Firm* — Patterson Thuente Christensen Pedersen, P.A.

(57) ABSTRACT

A device for application of energy within a tubular bodily structure including an optical fiber couplable to a source of laser energy and a guidewire tip. The optical fiber has a laser emitting portion remote from the source of laser energy and a distal end. The guidewire tip is operably secured to the optical fiber and extends distally outwardly away from the distal end of the optical fiber. The guidewire tip assists in advancing the device through the tubular bodily structure.

18 Claims, 7 Drawing Sheets

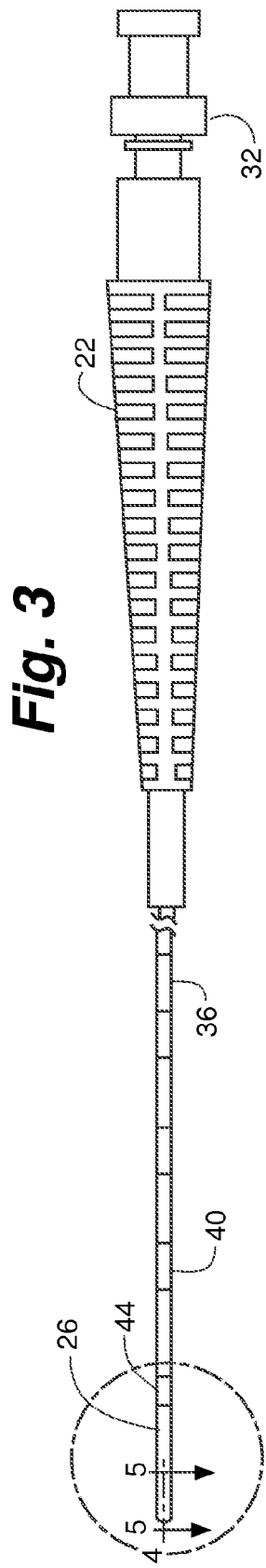

GUIDEWIRE TIPPED LASER FIBER

FIELD OF THE INVENTION

The present invention relates generally to the field of surgical instruments utilizing light application via optical fibers placed within the body. More particularly, the present invention relates to endovenous laser therapy of the peripheral veins, such as greater saphenous veins of the leg, for treatment of varicose veins.

BACKGROUND OF THE INVENTION

Varicose veins are enlarged, tortuous and often blue in color and commonly occur in the legs below the knee. Varicose veins are the most common peripheral vascular abnormality affecting the legs in the United States. Varicose veins often lead to symptomatic venous insufficiency. Greater saphenous vein reflux is the most common form of venous insufficiency in symptomatic patients and is frequently responsible for varicose veins in the lower leg. This occurs in about 25% of women and about 15% of men.

All veins in the human body have valves that when functioning properly, open to allow the flow of blood toward the heart and close to prevent backflow of blood toward the extremities. The backflow of blood is also known as reflux. The venous check valves perform their most important function in the veins of the legs where venous return flow is most affected by gravity. When the venous valves fail to function properly, blood leaks through the valves in a direction away from the heart and flows down the leg in the wrong direction. The blood then pools in the superficial veins under the skin resulting in the bulging appearance typically seen in varicose veins. The pooling of blood in the leg veins tends to stretch the thin elastic walls of the veins, which in turn causes greater disruption in the function of the valves, leading to worsening of the varicosities. When varicose veins become severe, the condition is referred to as chronic venous insufficiency. Chronic venous insufficiency can contribute to the development of pain, swelling, recurring inflammation, leg ulcers, hemorrhage and deep vein thrombosis.

Traditionally, varicose veins have been treated by a surgical procedure known as stripping. In stripping, varicose veins are ligated and completely removed. More recently, varicose veins have been treated by endovenous laser therapy. Endovenous laser therapy treats varicose veins of the leg by eliminating the highest point at which blood flows back down the veins, thereby cutting off the incompetent venous segment. Endovenous laser therapy has significant advantages over surgical ligation and stripping. In general, endovenous laser therapy has reduced risks related to anesthesia, less likelihood of surgical complications, reduced costs and a shorter recovery period than ligation and stripping.

Endovenous laser therapy involves the use of a bare tipped or shielded tip laser fiber to deliver laser energy to the venous wall from within the vein lumen that causes thermal vein wall damage at the desired location. The subsequent fibrosis at this location results in occlusion of the vein that prevents blood from flowing back down the vein. Generally, endovenous laser therapy utilizes an 810 to 980 nanometer diode laser as a source of laser energy that is delivered to the venous wall in a continuous mode with a power of about 10 to 15 Watts.

An exemplary endovenous laser therapy procedure is disclosed in U.S. Pat. No. 4,564,011 issued to Goldman. The Goldman patent discloses the use of an optical fiber to transmit laser energy into or adjacent to a blood vessel to cause clotting of blood within the vessel or to cause scarring and shrinkage of the blood vessel.

A typical endovenous laser therapy procedure includes the location and mapping of venous segments with duplex ultrasound. An introducer sheath is inserted into the greater saphenous vein over a guidewire, followed by a laser fiber about 600 micrometers in diameter. The distal end of the laser fiber is advanced to within 1 to 2 cm of the sapheno-femoral junction. Laser energy is then applied at a power level of about 10 to 15 watts along the course of the greater saphenous vein as the laser fiber is slowly withdrawn. Generally, positioning of the laser fiber is done under ultrasound guidance and confirmed by visualization of the red aiming beam of the laser fiber through the skin. The application of laser energy into the vein utilizes the hemoglobin in red blood cells as a chromophore. The absorption of laser energy by hemoglobin heats the blood to boiling, producing steam bubbles which cause full thickness thermal injury to the vein wall. This injury destroys the venous endothelium and creates a full-length occlusion and destruction of the greater saphenous vein. An example of current techniques for endovenous laser therapy procedures is described in U.S. Patent Publication No. 2003/0078569 A1, the disclosure of which is hereby incorporated by reference.

While current endovenous laser therapy procedures offer a number of advantages over conventional ligation and stripping, challenges remain in successfully implementing an endovenous laser therapy procedure. The accurate localization of the bare distal end of the laser fiber can be difficult even with ultrasound assistance. In addition, a bare distal end of the laser fiber is transparent to fluoroscopy. Because of the relatively small diameter and sharpness of the laser fiber, the distal tip of the laser fiber can sometimes enter or puncture and exit the vein wall while the laser fiber is being advanced up a tortuous greater saphenous vein. Laser fibers used in current endovenous laser therapy procedures are glass optical fibers coaxially surrounded by protective plastic jacket or coating.

In current endovenous laser therapy procedures, a laser fiber is inserted into a vein while sheathed in a catheter. Because of the relative stiffness of the laser fiber and the fact that it is formed from glass, and the relatively sharp distal end of the laser fiber, the catheter allows for easier advancing of the laser fiber through the blood vessel. When the laser fiber-catheter combination has reached a desired location, typically slightly proximal from the sapheno-femoral junction, the laser fiber is advanced to extend beyond the distal end of the catheter by a significant distance. Laser energy is applied through the optical fiber and the catheter and laser fiber are withdrawn at the same time that the laser energy is applied.

An alternative approach includes placing a guidewire in the blood vessel, advancing the guidewire until it is in a desired location, then advancing a laser fiber which includes a structure for engaging the guidewire, along the guidewire until it is at the desired location, withdrawing the guidewire and then withdrawing the laser fiber while simultaneously applying laser energy to the blood vessel. In either case, these procedures require the insertion and removal of multiple structures into and out of the blood vessel. These multiple insertions and removals take time, and may also increase the likelihood of possible unintended injury or perforation of the blood vessel during the procedure.

Thus, there is still room for improvement to endovenous laser procedure and apparatus.

SUMMARY OF THE INVENTION

The present invention solves many of the above discussed problems. The present invention includes a laser fiber for endovenous therapy having a shielded laser emitting section and a guidewire distal to the shielded laser emitting section. The invention generally includes a hub for coupling the optical fiber to a laser source, an optical fiber, an insulative tip shield, a tip sleeve that surrounds the insulative tip shield and a guidewire tip.

The hub in accordance with the present invention is generally conventional and includes a coupling to be coupled to a laser console laser source as well as a strain relief to minimize stress on the optical fiber when the optical fiber is flexed relative to the laser source. In one aspect of the invention, the optical fiber is a 600 micron optical fiber with a plastic jacket. The plastic jacket may be marked with ruler marks to facilitate withdrawing the optical fiber from a vein at a desired rate. The optical fiber also may include an insulative tip shield secured to the optical fiber at its distal most end. In one aspect of the invention, the optical tip shield may be formed of a ceramic material.

The tip sleeve in accordance with the present invention is a generally cylindrical structure dimensioned to surround the distal end of the optical fiber. The tip sleeve may be formed of a metallic material, for example, an alloy of about 90% platinum and about 10% iridium is one suitable material. If an insulative tip shield is present the may also surround the insulative tip shield.

The tip sleeve surrounds the distal end of the optical fiber and extends beyond the distal end of the optical fiber by a significant distance. The tip sleeve in accordance with the present invention may include a pair of opposed proximal slits and three distal slits that are located more distal than the proximal slits. In one aspect of the invention, the proximal slits have a length significantly greater than the distal slits. The tip sleeve may be secured to the optical fiber and to the guidewire tip, for example, by crimping. In addition, the tip sleeve may be secured to the guidewire tip by welding and to the optical fiber by adhesives such as high temperature adhesives.

The guidewire tip may be crimped or otherwise secured to the distal end of the tip sleeve. In one aspect of the invention, the guidewire tip may be formed of stainless steel and have a diameter of about 0.035 inches. The guidewire tip may be formed as a coil wire having a core ribbon. The guidewire tip generally includes ball welds on each end full round in shape. The guidewire tip may be straight or curved as is known in the arts of guidewires in general. The guidewire may be any flexible extension that extends beyond the distal end of the optical fiber and that facilitates atraumatic advancement of the optical fiber through as bodily lumen. The guidewire may be formed of metal, polymer or any other suitable material.

BRIEF DESCRIPTION OF THE DRAWINGS

FIG. 3 is a plan view of an optical fiber in accordance with the present invention.

DETAILED DESCRIPTION

Figure 1:
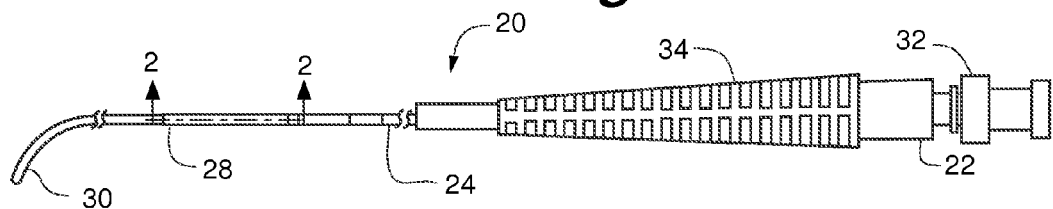
FIG. 1 is a plan view of a guidewire tipped optical fiber in accordance with the present invention.
Figure 2:
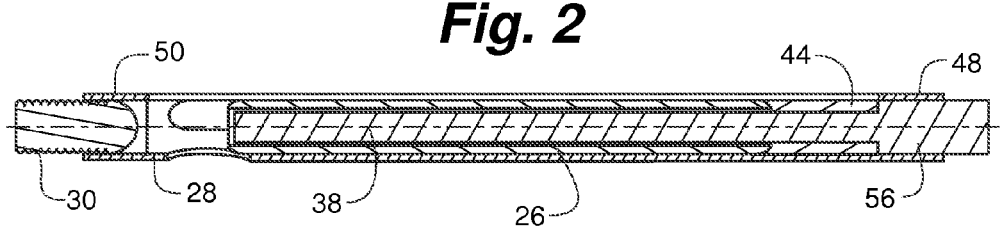
FIG. 2 is a cross sectional view of an optical fiber tip and tip sleeve in accordance with the present invention taken along section line 2-2 of FIG. 1.

Referring particularly to FIGS. 1 and 2, guidewire tip laser fiber 20 in accordance with the present invention, generally includes fiber hub 22, optical fiber 24, tip shield 26, tip sleeve 28 and guidewire tip 30. Starting from the most proximal end of guidewire tip laser fiber 20, in an example embodiment, fiber hub 22 is coupled to and surrounds optical fiber 24. The distal end of optical fiber 24 is surrounded by tip shield 26. Tip shield 26 is surrounded by tip sleeve 28, which terminates in guidewire tip 30.

Figure 7:
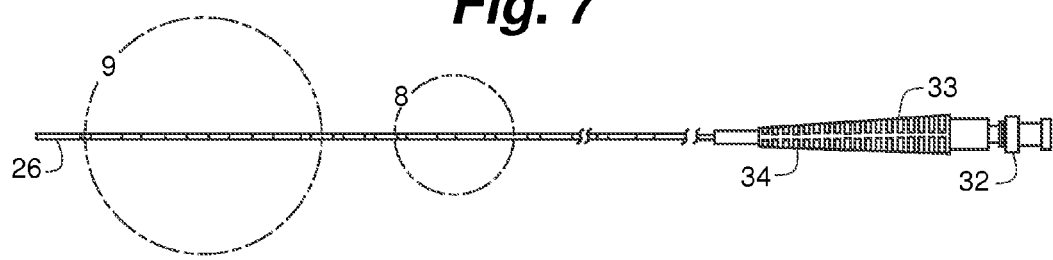
FIG. 7 is another plan view of optical fiber in accordance with the present invention.

Referring to FIGS. 1, 3 and 7, fiber hub 22 is generally conventional in structure and includes coupler 32 and strain relief 34. Coupler 32 is adapted to couple fiber hub 22 to a console laser source (not shown). Coupler 32 and strain relief 34 surround the proximal end of optical fiber 24. Coupler 32 can be a standardized connector such as an SMA-905 connector for connection to a laser source console (not shown).

In one aspect of the invention, optical fiber 24 is a 400-600 micron glass optical fiber having a finely polished distal tip end. However, a polymer fiber can be used as well. Those skilled in the art will understand that the designated dimensions of the glass optical fiber refers to the diameter D of the fiber including the fiber core and cladding but exclusive of protective jacket 36. The exterior dimensions of protective jacket 36 are larger. While a single optical fiber 24 is described herein, it should be understood that optical fiber 24 can also include a stranded arrangement of multiple optical fibers. Generally, optical fiber 24 is about 3.5 meters in length but this length should not be considered limiting.

The laser source console (not shown) may be, for example, a solid state diode laser console operating at a wave length of 810 nanometers, 940 nanometers or 980 nanometers and supporting a maximum power output of about 15 watts.

Protective jacket 36 coaxially surrounds optical fiber 24 throughout almost the entirety of its length. Protective jacket 36 is generally conventional in structure and may be formed from a biocompatible plastic material. Protective jacket 36 is removed from distal end 38 of optical fiber 24. Typically, about one half to two centimeters of protective jacket 36 is removed.

Figure 8:
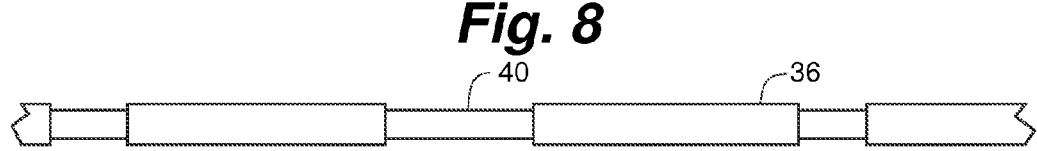
FIG. 8 is a detailed view taken at designated area 8 of FIG. 7.
Figure 9:
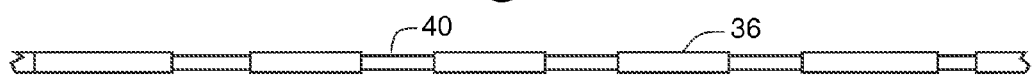
FIG. 9 is a detailed view taken at detail area 9 of FIG. 7.
Figure 10:
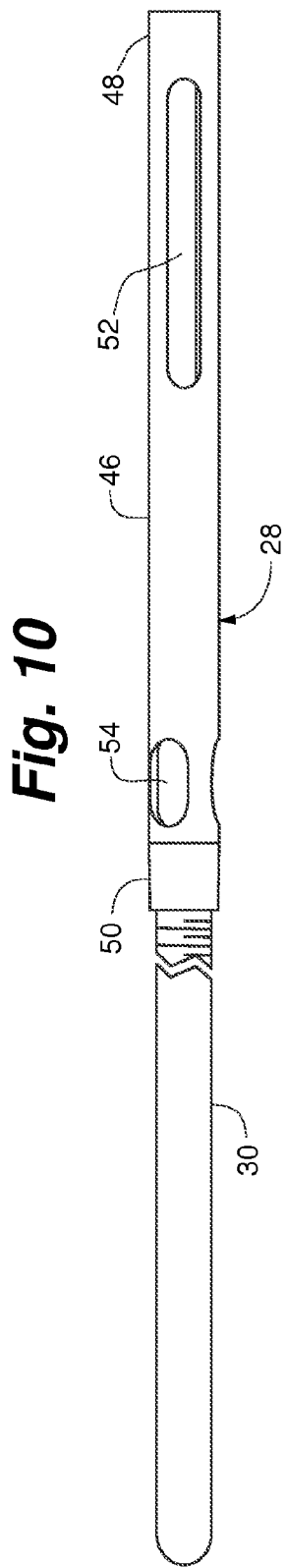
FIG. 10 is a plan view of a tip sleeve and guidewire portion in accordance with the present invention.
Figure 11:
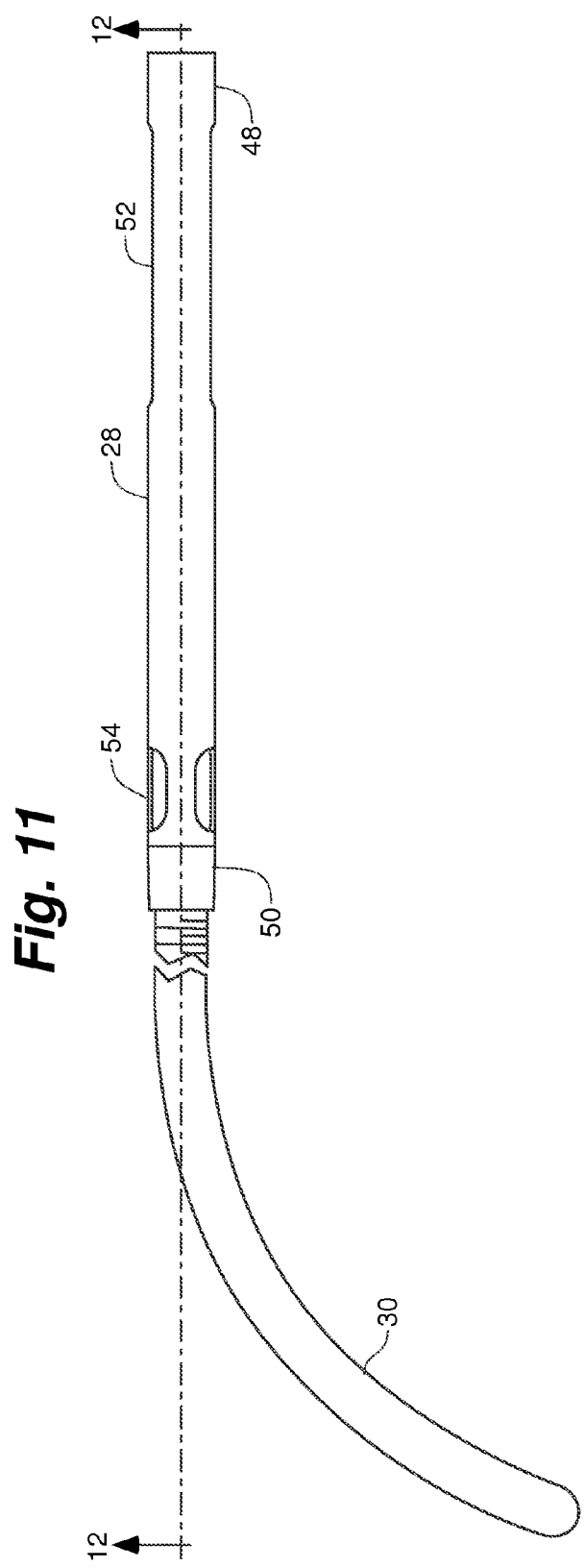
FIG. 11 is an elevational view of the tip sleeve and guidewire portion as depicted in FIG. 10.
Figure 12:
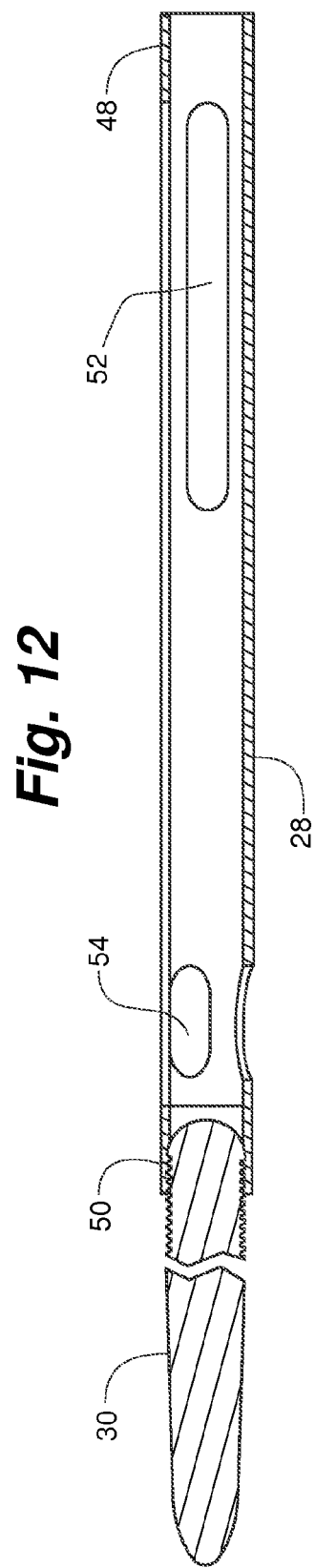
FIG. 12 is a cross sectional view taken along section line 12-12 of FIG. 11.
Figure 13:
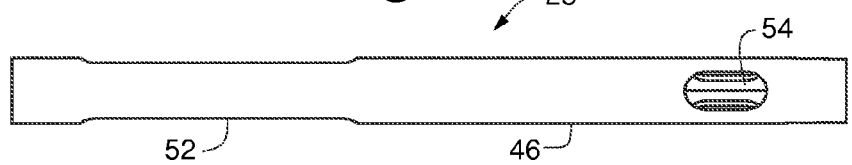
FIG. 13 is a plan view of a tip sleeve in accordance with the present invention.
Figure 14:
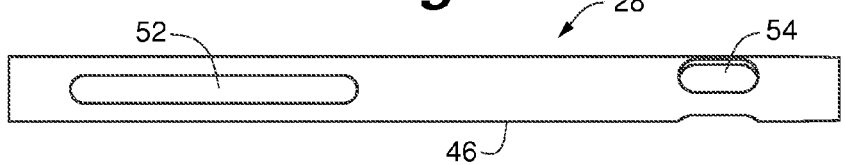
FIG. 14 is an elevational view of a tip sleeve in accordance with the present invention.
Figure 15:
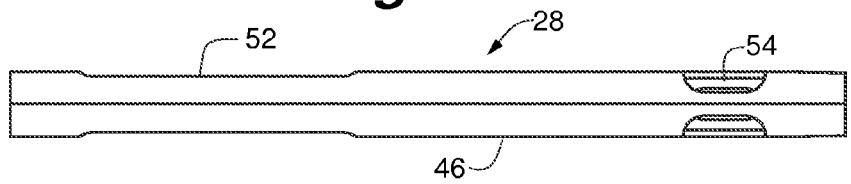
FIG. 15 is a bottom plan view of a tip sleeve in accordance with the present invention.
Figure 16:
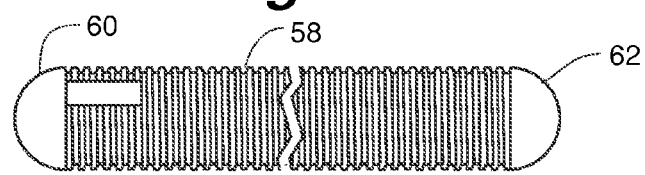
FIG. 16 is a plan view of a guidewire portion in accordance with the present invention.

Referring particularly to FIGS. 7, 8 and 9, protective jacket 36, in one embodiment of the present invention, is marked with printed scale 40. Printed scale 40 generally includes markings along the length of protective jacket 36, for example, every centimeter. Printed scale 40 may be numerically identified, for example, every centimeter or every 10 centimeters or some other selected interval. Printed scale 40 may extend over substantially the entire length of protective jacket 36 of optical fiber 24 or may be limited, for example, to the distal eighty to one hundred centimeters.

Figure 4:
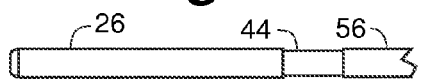
FIG. 4 is a detailed plan view taken at designated area 4 of FIG. 3.
Figure 5:
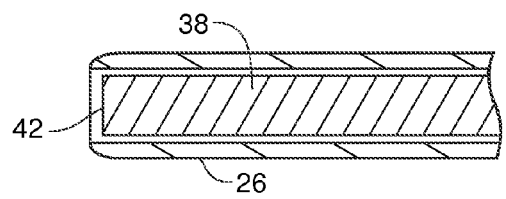
FIG. 5 is a cross sectional view taken along section lines 5-5 of FIG. 3.
Figure 6:
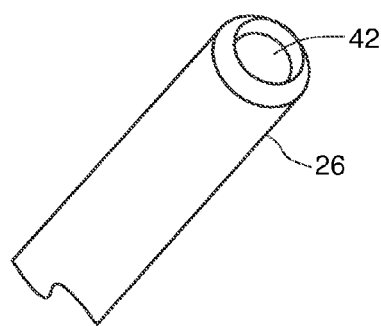
FIG. 6 is a perspective view of the insulative shielded tip of an optical fiber in accordance with the present invention.

Referring to FIGS. 2-6, tip shield 26 covers substantially the entire exposed distal end 38 of optical fiber 24. Tip shield 26 coaxially surrounds distal end 38 of optical fiber 24 while leaving distal tip face 42 exposed. Tip shield 26 may be formed of a rigid heat resistant insulative material such as ceramic or carbon. In one aspect of the invention, tip shield 26 extends slightly beyond distal tip face 42 of optical fiber 24. Thus, distal tip face 42 of optical fiber 24 is recessed into tip shield 26 for example 0.005 inches plus or minus 0.003. This relationship is can be seen in FIGS. 5-6.

Referring to FIG. 4, tip shield 26 may be secured to optical fiber 24, for example, by the use of high temperature adhesive 44.

Referring to FIG. 2, and 10-15, tip sleeve 28, in one embodiment of the invention, is a generally tubular cylindrical structure generally including body 46, proximal crimp portion 48, distal crimp portion 50, proximal openings 52 and distal openings 54.

Body 46 of tip shield 26 is a generally cylindrical structure which may be formed of a metallic material. In one embodiment of the invention, tip shield 26 may be formed of an alloy of approximately 90% platinum and 10% iridium. Body 46 is generally cylindrical in shape and is sized to fit over optical fiber 24 and tip shield 26 in a closely fitting relationship.

Proximal crimp portion 48 is positioned to cover distal jacket portion 56 of optical fiber 24. Proximal crimp portion 48 may then be crimped or otherwise secured to distal jacket portion 56. Proximal crimp portion 48 in one embodiment of the invention has a length of approximately one half millimeter.

Distal crimp portion 50 is sized to closely receive guidewire tip 30 therein. Distal crimp portion 50 may be secured to guidewire tip 30 by crimping or other fastening techniques such as welding.

Proximal openings 52 in one aspect of the invention are located near the proximal end of body 46 of tip shield 26. In one aspect of the invention, proximal openings 52 may take the form of two elongate slits positioned opposite one another and extending lengthwise along body 46.

In one embodiment of the invention, proximal openings 52 may have a length approximately 30% of the length of tip shield 26. In one aspect of the invention, proximal openings 52 may be positioned to expose a proximal part of tip shield 26 and a portion of high temperatures adhesive 44. As depicted, proximal openings 52 are positioned to be outside of proximal crimp portion 48.

Distal openings 54, in one aspect of the invention, are located proximal to and outside of distal crimp portion 50. In one embodiment of the invention, distal openings 54 include three openings distributed evenly about the circumference of body 46. Distal openings 54 in one aspect of the invention may have a length approximately five percent of the length of body 46. Distal openings 54 in one aspect of the invention, are positioned to be located approximately at the distal end of tip shield 26, and to extend beyond the distal end of tip shield 26 for a significant portion of their length.

Referring particularly to FIGS. 1, 10, 11, 12 and 16, guidewire tip 30 generally includes coil portion 58, distal ball weld 60 and proximal ball weld 62. Guidewire tip 30 may be straight, curved, bent, flexible, floppy, adjustable or non-adjustable similar to guidewires known in the guidewire arts. Guidewire tip 30 is sized to fit into distal crimp portion 50 of tip sleeve 28.

Figure 17:
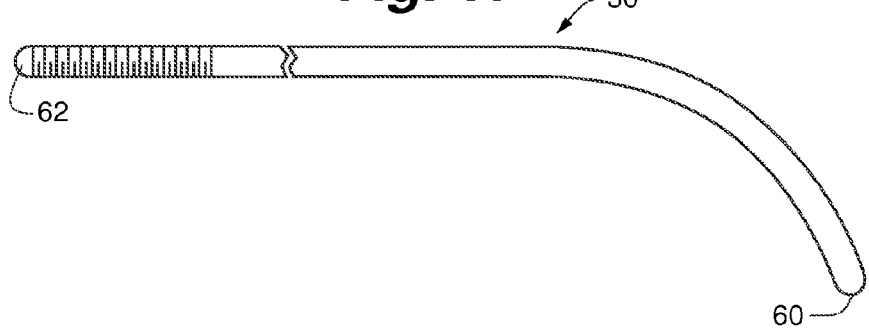
FIG. 17 is plain view of a cyrved guidewire in accordance with the present invention.

Referring to FIG. 17, in one example embodiment, guidewire tip 30 may be curved as pictured. Many other embodiments and shapes of guidewire tip 30 may be presented as well.

In operation, a physician prepares a laser console (not shown) in accordance with its operating instructions, and verifies that the guidewire tipped laser fiber 20 is properly connected to the laser console. The physician then maps the vessel treatment area using duplex ultrasound, being careful to mark the vessel location on the patient's skin for guiding treatment. The physician then preps and drapes the limb in sterile fashion and wraps the ultra sound transducer with a sterile cover. Using sterile technique, the physician opens the guidewire tipped laser fiber 20 and, if used, an introducer needle into the sterile field.

The physician can cannulate the vessel to be treated using a surgical cut down or the introducer needle. The guidewire tipped laser fiber 20 is inserted into the vessel through the incision or needle. If a needle is used, it is removed from the vessel. The guidewire tip laser fiber 20 is advanced through the vessel to the desired treatment site. The tip sleeve 28 in combination with the tip shield 26 prevents the vessel wall from contacting the optical fiber 24. Guidewire tip 30 assists in advancing guidewire tip laser fiber 20 without the need for a catheter or separate guidewire. Anesthetic is delivered to bathe the surrounding tissue with dilute anesthetic to provide thermal protection.

The physician places the laser console in the ready mode and sets the power level to settings for the procedure. The physician holds the optical fiber 24 and activates the laser typically by stepping on a foot pedal. The physician then simultaneously withdraws the guidewire tip laser fiber 20 while delivering approximately 50-70 jewels per centimeter of laser energy. The physician should not compress or attempt to place the fiber in contact with the vein wall.

After the procedure is complete, the laser is turned to standby, guidewire tipped laser fiber 20 is removed from the blood vessel and compression is held on the wound until bleeding stops. A hemostatic bandage may be applied over the vessel entry site, and a compression stocking may also be applied over the entire treatment site length. The patient is then cared for under normal post-operative procedures and follow-up exams are scheduled as needed.

When guidewire tipped laser fiber 20 in inserted into a vein blood enters distal openings 54 and fills the interior of body 46 distal to distal tip face 42 of optical fiber 24. Upon application of laser energy the blood is heated and gaseous products of the application to laser energy to the blood are expelled from the interior of body 46 through distal openings 54. Tip sleeve 28 and guidewire tip 30 are also heated and transmit energy to the blood.

The present invention may be embodied in other specific forms without departing from the spirit of the essential attributes thereof, therefore, the illustrated embodiments should be considered in all respects as illustrative and not restrictive, reference being made to the appended claims rather than to the forgoing description to indicate the scope of the invention.

The invention claimed is:

1. A device for application of energy within a tubular bodily structure, comprising:
   an optical fiber couplable to a source of laser energy at a proximal end of the optical fiber, the optical fiber having a laser emitting portion that is located remotely from the source of laser energy and the optical fiber also having a distal end, the laser emitting portion and the distal end being enclosed in a tip sleeve having openings therein; and a metallic guidewire tip operably secured to the optical fiber via the tip sleeve and extending distally outwardly away from and distally beyond the distal end of the optical fiber whereby the guidewire tip assists in advancing the device through the tubular bodily structure.

2. The device as claimed in claim 1, wherein the tip sleeve is operably secured to and at least partially surrounding the distal end of the optical fiber.

3. The device as claimed in claim 2, wherein the guidewire tip is operably coupled to the tip sleeve.

4. The device as claimed in claim 2, wherein the tip sleeve comprises a generally cylindrical body having at least one opening therein.

5. The device as claimed in claim 1, further comprising an insulative tip shield at least partially surrounding the laser emitting portion.

6. The device as claimed in claim 1, wherein the guidewire tip is curved.

7. A method of insertion and advancement of a device for application of energy within a tubular bodily structure, comprising:

accessing the tubular bodily structure;

coupling an optical fiber to a source of laser energy, the optical fiber having a laser emitting portion remote from the source of laser energy and a distal end both enclosed in a tip sleeve having openings therein; and advancing a guidewire tip operably secured to the optical fiber via the tip sleeve and extending distally outwardly away from and distally beyond the distal end of the optical fiber into and through the tubular bodily structure without use of a catheter.

8. The method as claimed in claim 7, wherein accessing the tubular bodily structure further comprises cutting down surgically to the tubular bodily structure.

9. The method as claimed in claim 7, wherein accessing the tubular bodily structure further comprises inserting a hollow needle into the tubular bodily structure.

10. A device for application of energy within a tubular bodily structure, comprising:

an optical fiber couplable to a source of laser energy, the optical fiber having a laser emitting portion remote from the source of laser energy and the optical fiber also having a distal end, the laser emitting portion and the distal end being enclosed in a tip sleeve having openings therein; and means for guiding that are operably secured to the optical fiber via the tip sleeve and that extend distally outwardly away from the distal end of the optical fiber whereby the means for guiding assists in advancing the device through the tubular bodily structure.

11. The device as claimed in claim 10, wherein the tip sleeve comprises a generally cylindrical body having at least one opening therein.

12. The device as claimed in claim 10, further comprising means for insulating at least partially surrounding the laser emitting portion.

13. The device as claimed in claim 10, wherein the means for guiding is curved.

14. A device for application of energy within a tubular bodily structure, comprising:

an optical fiber couplable to a source of laser energy, the optical fiber having a laser emitting portion remote from the source of laser energy and the optical fiber also having a distal end, the laser emitting portion and the distal end being enclosed in a tip sleeve having openings therein; and a resiliently flexible guidewire portion operably secured to the optical fiber via the tip sleeve and extending distally outwardly away from and distally beyond the distal end of the optical fiber whereby the flexible guide portion assists in advancing the device through the tubular bodily structure.

15. The device as claimed in claim 14, wherein the tip sleeve member is operably secured to and at least partially surrounds the distal end of the optical fiber.

16. The device as claimed in claim 15, wherein the sleeve member comprises a generally cylindrical body having at least one opening therein.

17. The device as claimed in claim 14, further comprising an insulative tip shield at least partially surrounding the laser emitting portion.

18. The device as claimed in claim 14, wherein the resilient guidewire portion is curved.

* * * * *